(12) United States Patent
Schmidt et al.

(10) Patent No.: US 9,480,850 B2
(45) Date of Patent: Nov. 1, 2016

(54) LEADLESS CARDIAC PACEMAKER AND RETRIEVAL DEVICE

(71) Applicant: Cardiac Pacemakers, Inc., St. Paul, MN (US)

(72) Inventors: Brian L. Schmidt, White Bear Lake, MN (US); Benjamin J. Haasl, Forest Lake, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 191 days.

(21) Appl. No.: 14/451,564

(22) Filed: Aug. 5, 2014

(65) Prior Publication Data

US 2015/0051610 A1    Feb. 19, 2015

Related U.S. Application Data

(60) Provisional application No. 61/866,633, filed on Aug. 16, 2013.

(51) Int. Cl.
*A61B 19/00* (2006.01)
*A61N 1/375* (2006.01)
(Continued)

(52) U.S. Cl.
CPC .............. *A61N 1/3756* (2013.01); *A61N 1/362* (2013.01); *A61N 1/37205* (2013.01)

(58) Field of Classification Search
CPC .......... A61F 2002/011; A61F 2/2427; A61B 2017/22035; A61B 17/221; A61B 5/686; A61B 5/0215; A61N 1/3756; A61N 1/37205; A61N 2001/0578; A61N 1/362; A61N 1/0573; A61N 1/059; A61N 1/372; A61N 2001/058; A61N 1/057; A61N 1/0587

USPC ......... 600/373; 606/127, 129; 607/122, 126, 607/127, 128

See application file for complete search history.

(56) References Cited

U.S. PATENT DOCUMENTS

| | | |
|---|---|---|
| 721,869 A | 3/1903 | Dunning |
| 3,717,151 A | 2/1973 | Collett |

(Continued)

FOREIGN PATENT DOCUMENTS

| | | |
|---|---|---|
| CA | 1003904 A1 | 1/1977 |
| DE | 2053919 A1 | 5/1972 |

(Continued)

OTHER PUBLICATIONS

Spickler, et al. "Totally Self-Contained Intracardiac Pacemaker" J. Electrocardiology, vol. 3, Nos. 3 & 4, pp. 325-331 (1970).

*Primary Examiner* — Katherine M Shi
(74) *Attorney, Agent, or Firm* — Seager, Tufte & Wickhem LLP

(57) ABSTRACT

A retrieval device and an associated implantable cardiac pacing device. The retrieval device includes a grasping mechanism configured to capture a docking member of the implantable cardiac pacing device to draw the implantable cardiac pacing device into the lumen of a retrieval catheter. The grasping mechanism is expandable from a first position to a second position and is biased toward the first position in an equilibrium condition. The grasping mechanism is configured to surround and pass over a head portion of the docking member in the second position, and be contracted toward the first position to capture the docking member with the grasping mechanism.

12 Claims, 16 Drawing Sheets

(51) Int. Cl.
*A61N 1/362* (2006.01)
*A61N 1/372* (2006.01)

(56) References Cited

U.S. PATENT DOCUMENTS

| | | | |
|---|---|---|---|
| 3,754,555 A | 8/1973 | Schmitt |
| 3,814,104 A | 6/1974 | Irnich et al. |
| 3,835,864 A | 9/1974 | Rasor et al. |
| 3,902,501 A | 9/1975 | Citron et al. |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bornzin |
| 4,662,382 A | 5/1987 | Sluetz et al. |
| 4,898,577 A | 2/1990 | Badger et al. |
| 4,913,164 A | 4/1990 | Greene et al. |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,562,723 A | 10/1996 | Rugland et al. |
| 5,575,814 A | 11/1996 | Giele et al. |
| 5,578,068 A | 11/1996 | Laske et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,041,258 A | 3/2000 | Cigaina et al. |
| 6,055,457 A | 4/2000 | Bonner |
| 6,074,401 A | 6/2000 | Gardiner et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,743,240 B2 | 6/2004 | Smith et al. |
| 6,755,812 B2 | 6/2004 | Peterson et al. |
| 6,909,920 B2 | 6/2005 | Lokhoff et al. |
| 6,944,507 B2 | 9/2005 | Froberg et al. |
| 6,953,454 B2 | 10/2005 | Peterson et al. |
| 7,027,876 B2 | 4/2006 | Casavant et al. |
| 7,082,335 B2 | 7/2006 | Klein et al. |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,383,091 B1 | 6/2008 | Chitre et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |
| 7,558,631 B2 | 7/2009 | Cowan et al. |
| 7,634,319 B2 | 12/2009 | Schneider et al. |
| 7,647,109 B2 | 1/2010 | Hastings et al. |
| 7,657,325 B2 | 2/2010 | Williams |
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |
| 7,890,186 B2 | 2/2011 | Wardle et al. |
| 7,904,179 B2 | 3/2011 | Rutten et al. |
| 7,920,928 B1 | 4/2011 | Yang et al. |
| 7,993,351 B2 | 8/2011 | Worley et al. |
| 8,010,209 B2 | 8/2011 | Jacobson |
| 8,036,757 B2 | 10/2011 | Worley |
| 8,057,486 B2 | 11/2011 | Hansen |
| 8,082,035 B2 | 12/2011 | Glukhovsky |
| 8,103,361 B2 | 1/2012 | Moser |
| 8,108,054 B2 | 1/2012 | Helland |
| 8,142,347 B2 | 3/2012 | Griego et al. |
| 8,160,722 B2 | 4/2012 | Rutten et al. |
| 8,185,213 B2 | 5/2012 | Kveen et al. |

(56) References Cited

U.S. PATENT DOCUMENTS

| | | | |
|---|---|---|---|
| 8,219,213 B2 | 7/2012 | Sommer et al. |
| 8,233,994 B2 | 7/2012 | Sommer et al. |
| 8,252,019 B2 | 8/2012 | Fleming, III |
| 8,295,939 B2 | 10/2012 | Jacobson |
| 8,313,445 B2 | 11/2012 | Mishima et al. |
| 8,352,025 B2 | 1/2013 | Jacobson |
| 8,352,028 B2 | 1/2013 | Wenger |
| 8,364,277 B2 | 1/2013 | Glukhovsky |
| 8,364,280 B2 | 1/2013 | Marnfeldt et al. |
| 8,406,900 B2 | 3/2013 | Barlov et al. |
| 8,406,901 B2 | 3/2013 | Starkebaum et al. |
| 8,428,750 B2 | 4/2013 | Kolberg |
| 8,452,420 B2 | 5/2013 | Flach et al. |
| 8,478,431 B2 | 7/2013 | Griswold et al. |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan et al. |
| 8,634,912 B2 | 1/2014 | Bornzin et al. |
| 8,670,842 B1 | 3/2014 | Bornzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 2002/0077556 A1 | 6/2002 | Schwartz |
| 2003/0004537 A1 | 1/2003 | Boyle et al. |
| 2004/0176797 A1 | 9/2004 | Opolski |
| 2005/0090890 A1 | 4/2005 | Wu et al. |
| 2005/0267555 A1 | 12/2005 | Marnfeldt et al. |
| 2006/0247753 A1 | 11/2006 | Wenger et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart |
| 2007/0293904 A1 | 12/2007 | Gelbart |
| 2008/0021532 A1 | 1/2008 | Kveen et al. |
| 2008/0051706 A1* | 2/2008 | Hirszowicz ...... A61B 17/22032 604/103.03 |
| 2009/0082828 A1 | 3/2009 | Ostroff |
| 2009/0281605 A1 | 11/2009 | Marnfeldt et al. |
| 2010/0198288 A1 | 8/2010 | Ostroff |
| 2011/0034939 A1 | 2/2011 | Kveen et al. |
| 2011/0112548 A1 | 5/2011 | Fifer et al. |
| 2011/0125163 A1 | 5/2011 | Rutten et al. |
| 2011/0190785 A1 | 8/2011 | Gerber et al. |
| 2011/0190786 A1 | 8/2011 | Gerber et al. |
| 2011/0208260 A1 | 8/2011 | Jacobson |
| 2011/0237967 A1 | 9/2011 | Moore et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0143239 A1* | 6/2012 | Aklog ............... A61B 17/3207 606/200 |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103049 A1 | 4/2013 | Bonde |
| 2013/0116741 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2014/0058494 A1 | 2/2014 | Ostroff et al. |
| 2014/0074114 A1 | 3/2014 | Khairkhahan et al. |
| 2014/0148815 A1 | 5/2014 | Wenzel et al. |
| 2014/0180306 A1 | 6/2014 | Grubac et al. |

FOREIGN PATENT DOCUMENTS

| | | |
|---|---|---|
| EP | 779080 B1 | 5/2003 |
| JP | 05245215 A | 9/1993 |
| WO | 03032807 A2 | 4/2003 |
| WO | 2009039400 A1 | 3/2009 |
| WO | 2012092067 A1 | 7/2012 |
| WO | 2012092074 A1 | 7/2012 |

* cited by examiner

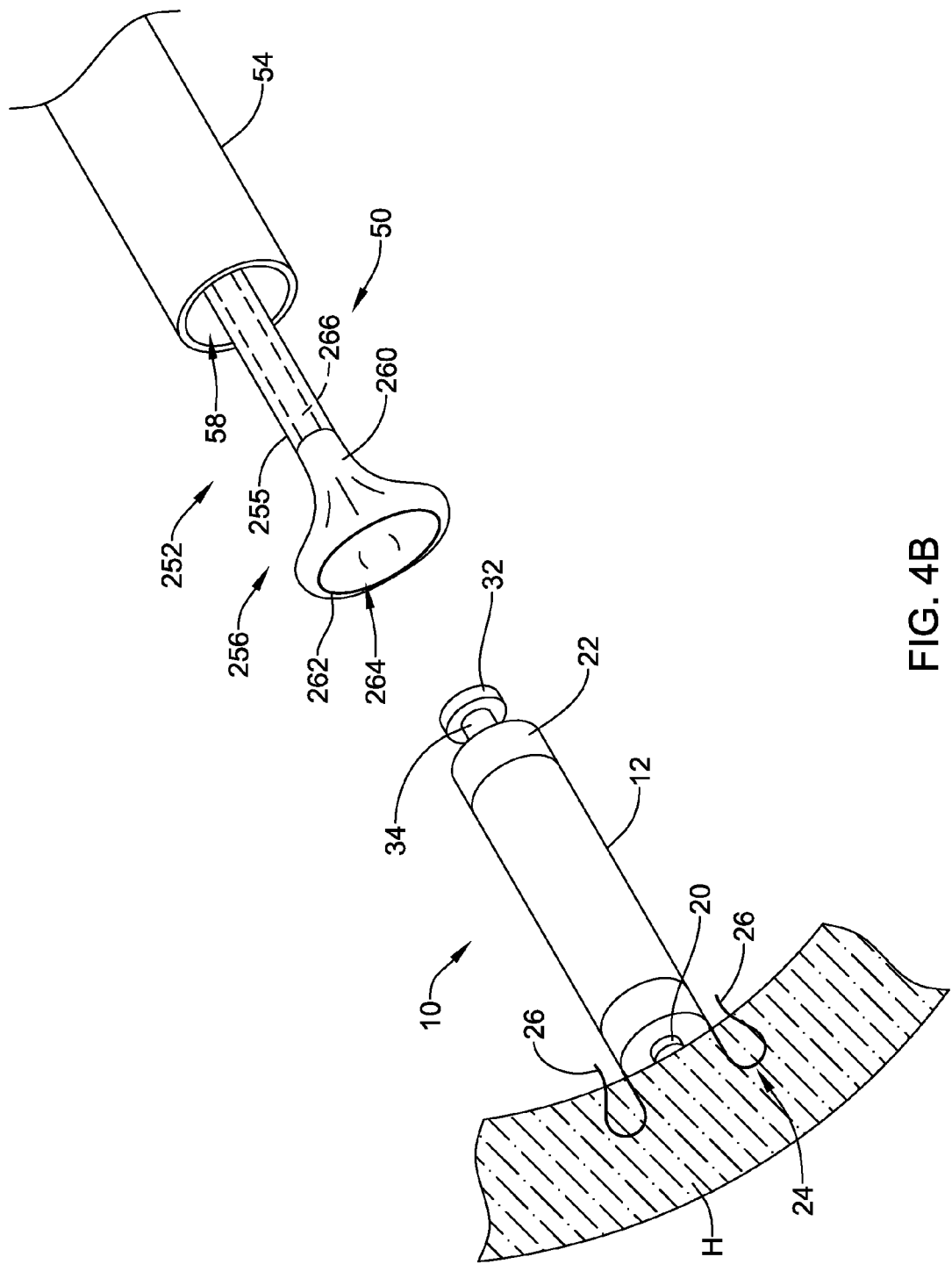

LEADLESS CARDIAC PACEMAKER AND RETRIEVAL DEVICE

CROSS-REFERENCES TO RELATED APPLICATIONS

This application claims the benefit of U.S. Provisional Application No. 61/866,633 filed Aug. 16, 2013, the complete disclosure of which is herein incorporated by reference.

TECHNICAL FIELD

The disclosure is directed to implantable cardiac devices and associated retrieval devices. More particularly, the disclosure is directed to leadless cardiac stimulators or pacemakers having proximal docking members and associated retrieval devices including retrieval mechanisms configured to engage the docking members.

BACKGROUND

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber with a fixation mechanism engaging the intracardiac tissue. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition.

Accordingly, there it is desirable to provide alternative structures, assemblies and systems for retrieving leadless cardiac pacemakers from an implantation site in a heart chamber.

SUMMARY

The disclosure is directed to several alternative designs, materials and methods of manufacturing medical device structures and assemblies, and uses thereof.

Accordingly, one illustrative embodiment is an assembly for retrieving an implantable cardiac pacing device. The assembly includes an implantable cardiac pacing device and an associated retrieval system. The implantable cardiac pacing device has a housing, an electrode positioned proximate a distal end of the housing, and a docking member extending from a proximal end of the housing opposite the distal end The docking member includes a head portion and a neck portion extending between the housing and the head portion. The retrieval system includes a retrieval catheter and a retrieval device advanceable from the distal end of the retrieval catheter. The retrieval device has a grasping mechanism configured to capture the docking member to draw the implantable cardiac pacing device into the lumen of the retrieval catheter. The grasping mechanism is expandable from a first position to a second position. The grasping mechanism is biased toward the first position in an equilibrium condition. The grasping mechanism is configured to surround and pass over the head portion of the docking member in the second position, and be contracted toward the first position to capture the docking member with the grasping mechanism.

Another illustrative embodiment is a method of retrieving an implantable cardiac pacing device from a heart. The implantable cardiac pacing device has a housing having a longitudinal axis, an electrode positioned proximate a distal end of the housing, and a docking member extending from a proximal end of the housing opposite the distal end. The docking member includes a head portion and a neck portion extending between the housing and the head portion, the head portion having a radial dimension from the longitudinal axis and the neck portion having a radial dimension from the longitudinal axis less than the radial dimension of the head portion. The method includes advancing a retrieval system into a heart having the implantable cardiac pacing device implanted therein. The retrieval system includes a retrieval catheter having a lumen therein and a retrieval device advanceable from a distal end of the retrieval catheter. The retrieval device includes a grasping mechanism expandable from a first position to a second position. The grasping mechanism is biased toward the first position in an equilibrium condition. The grasping mechanism is expanded to the second position and the grasping mechanism is advanced, in the second position, toward the docking member such that the head portion of the docking member passes through an opening of the grasping mechanism. The grasping mechanism is then contracted toward the first position to lock the grasping mechanism to the docking member. The retrieval device is then retracted proximally to draw the implantable cardiac pacing device into the lumen of the retrieval catheter.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIGS. 4A-4D are perspective views of another exemplary retrieval device and associate method of retrieving an implantable device.

Figure 1:
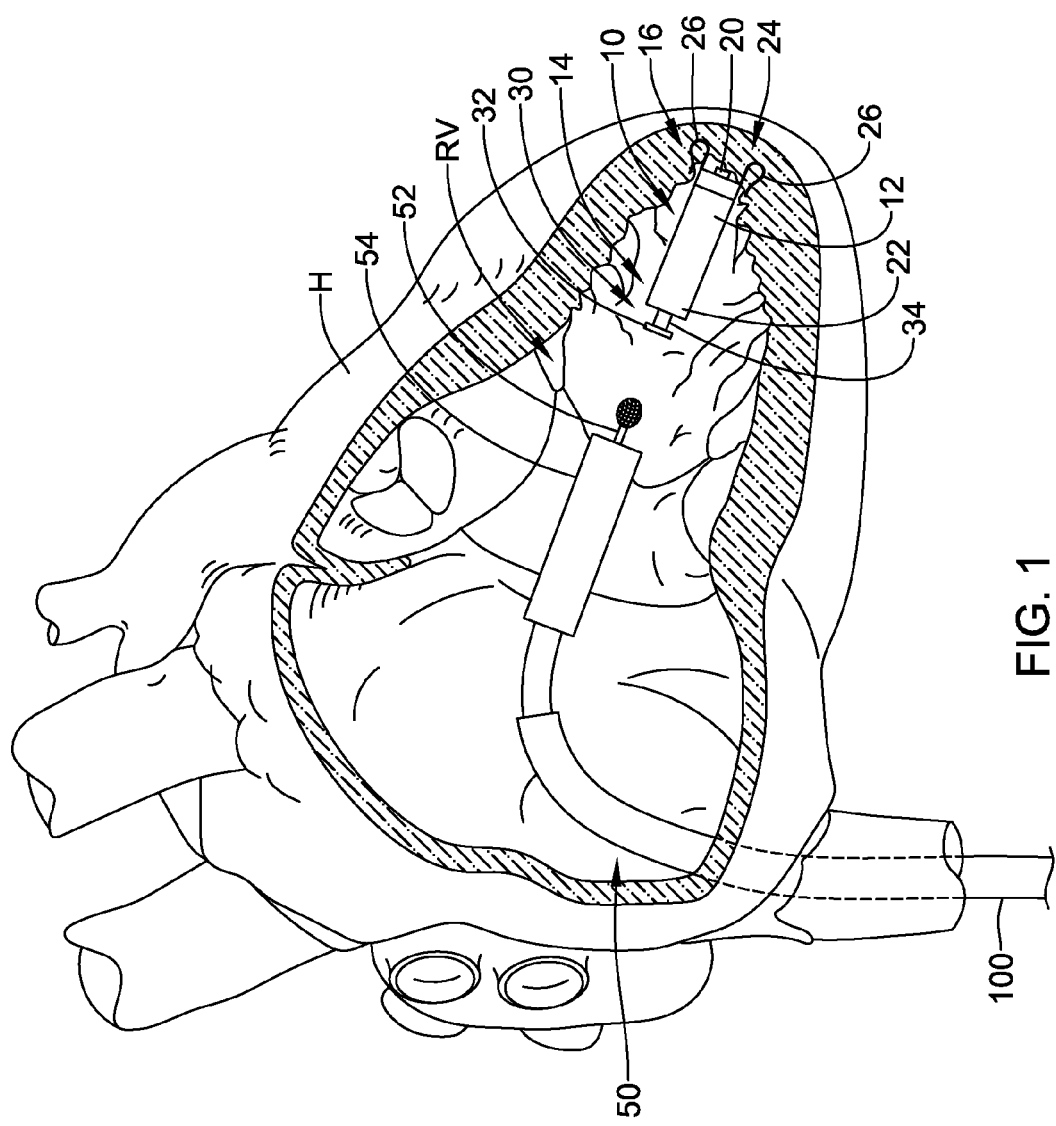
FIG. 1 illustrates an exemplary implantable device implanted in a chamber of a heart and an associated retrieval device retrieving the implantable device during a retrieval procedure.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Referring to FIG. 1, an exemplary implantable leadless cardiac pacing device 10 (e.g., a leadless pacemaker) is illustrated implanted in a chamber of a heart H, such as the apex of the right ventricle RV. The implantable device 10 may include a shell or housing 12 having a proximal end 14 and a distal end 16. The implantable device 10 may include a first electrode 20 positioned proximate the distal end 16 of the housing 12 and a second electrode 22 positioned proximate the proximal end 14 of the housing 12. The electrodes 20, 22 may be sensing and/or pacing electrodes to provide electro-therapy and/or sensing capabilities. The first electrode 20 may be configured to be positioned against or otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion from the longitudinal axis of the implantable device 10. The docking member 30 may be configured to facilitate delivery of the implantable device 10 to the intracardiac site and/or retrieval of the implantable device 10 from the intracardiac site. Some exemplary embodiments of the docking member 30 are described in further detail herein.

If it is desired to retrieve the implantable device 10 from the heart H, a retrieval system 50 may be advanced into the chamber of the heart H to capture the implantable device 10 and remove the implantable device 10 from the heart H. The retrieval system 50 may be advanced into the right ventricle RV of the heart H, using any desired route. For example, the retrieval system 50 may be through the femoral vein from a femoral access site, through the inferior vena cava, into the right atrium, and through the tricuspid valve into the right ventricle RV. It is noted, however, other pathways may be implemented, if desired.

One exemplary retrieval system 50 is illustrated in FIG. 1. The retrieval system 50 may include a retrieval device 52 advanceable from a lumen of a retrieval catheter 54. In some instances, as shown in FIG. 1, the retrieval catheter 54 may include an elongate shaft having an enlarged distal portion to receive the implantable device 10 therein. In some instances, the retrieval system 50 may also include a guide catheter 100, such as a steerable guide catheter or a guide catheter having a fixed or preset curvature, to facilitate directing the retrieval catheter 54 and/or the retrieval device 52 toward the implantable device 10 in the chamber of the heart H.

The retrieval device 52 may include a grasping mechanism extending from a distal end of the retrieval device 52 configured to engage the docking member 30 of the implantable device 10. Once the grasping mechanism of the retrieval device 52 has captured the docking member 30, the retrieval device 52 may be actuated proximally relative to the retrieval catheter 54 to pull the implantable device 10 into the lumen of the retrieval catheter 54. The enlarged size of the head portion 32 relative to the neck portion 34 may permit the grasping mechanism of the retrieval device 52 to encircle the neck portion 34 below (i.e., distal of) the head portion 32 and retain the loop 122 around the docking member 30 as the retrieval device 52 is pulled proximally. As the implantable device 10 is pulled into the retrieval catheter 54, the fixation mechanism 24 may disengage from the heart tissue to detach the implantable device 10 from the heart wall. For example, the hooks 26 may elongate as the implantable device 10 is drawn proximally into the lumen of the retrieval catheter 54.

In some instances, the grasping mechanism may be expandable from a first position to a second position. The grasping mechanism may be configured to be delivered to the chamber of the heart H while in the first position. The grasping mechanism may be configured to surround and pass over the head portion 32 of the docking member 30 in the second position, and then contracted toward the first position to capture the docking member 30 with the grasping mechanism. In some instances, the grasping mechanism may be biased toward the first position in an equilibrium condition. In other words, in the absence of an external force, the grasping mechanism may be configured to revert to or toward the first position.

Turning to FIGS. 2A-2D, an exemplary embodiment of a retrieval device 52 and associate method of retrieving an implantable device 10 is shown. The retrieval device 52 may be extendable distally from a lumen 58 of the retrieval catheter 54 toward the docking member 30 of the implantable device 10. The retrieval device 52 may include an elongate shaft 55 and a grasping mechanism 56 positioned at the distal end of the elongate shaft 55. The grasping mechanism 56 may be expandable from a first position, shown in FIG. 2A, to a second position, shown in FIG. 2B, and then contracted toward the first position, shown in FIG. 2D, to capture the docking member 30 with the grasping mechanism 56.

The grasping mechanism 56 may include an inflatable balloon 60 secured to the distal end of the elongate shaft 55 of the retrieval device 52 and a mesh 62 formed of a plurality of filaments surrounding the balloon 60. The filaments of the mesh 62 may be arranged in any desired manner to provide openings between adjacent filaments. For example, the filaments may be woven, braided, knitted, or otherwise arranged in an intersecting or interconnected arrangement to provide openings between adjacent filaments.

Figure 2A:
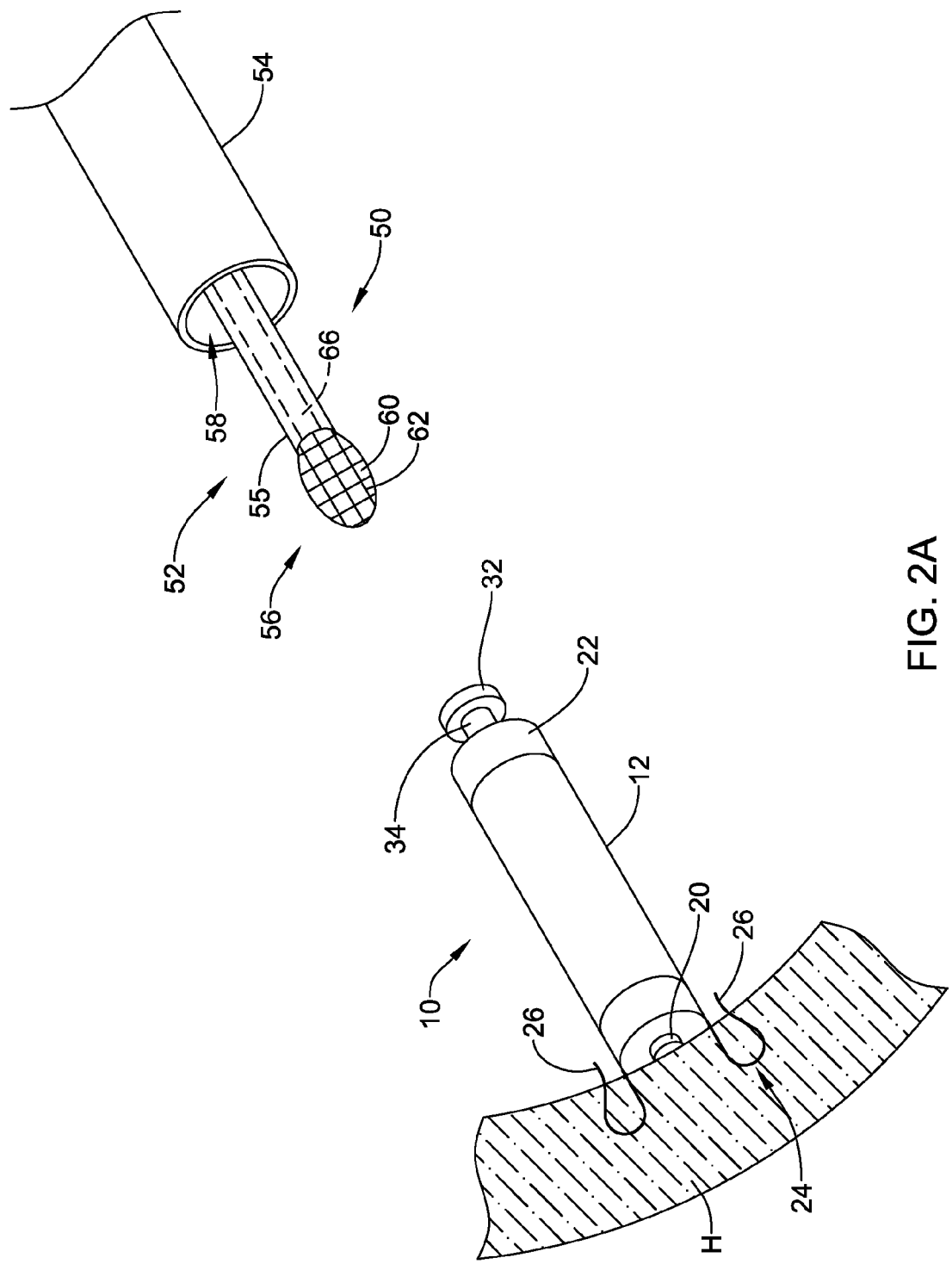
FIGS. 2A-2D are perspective views of an exemplary retrieval device and associate method of retrieving an implantable device.
Figure 2B:
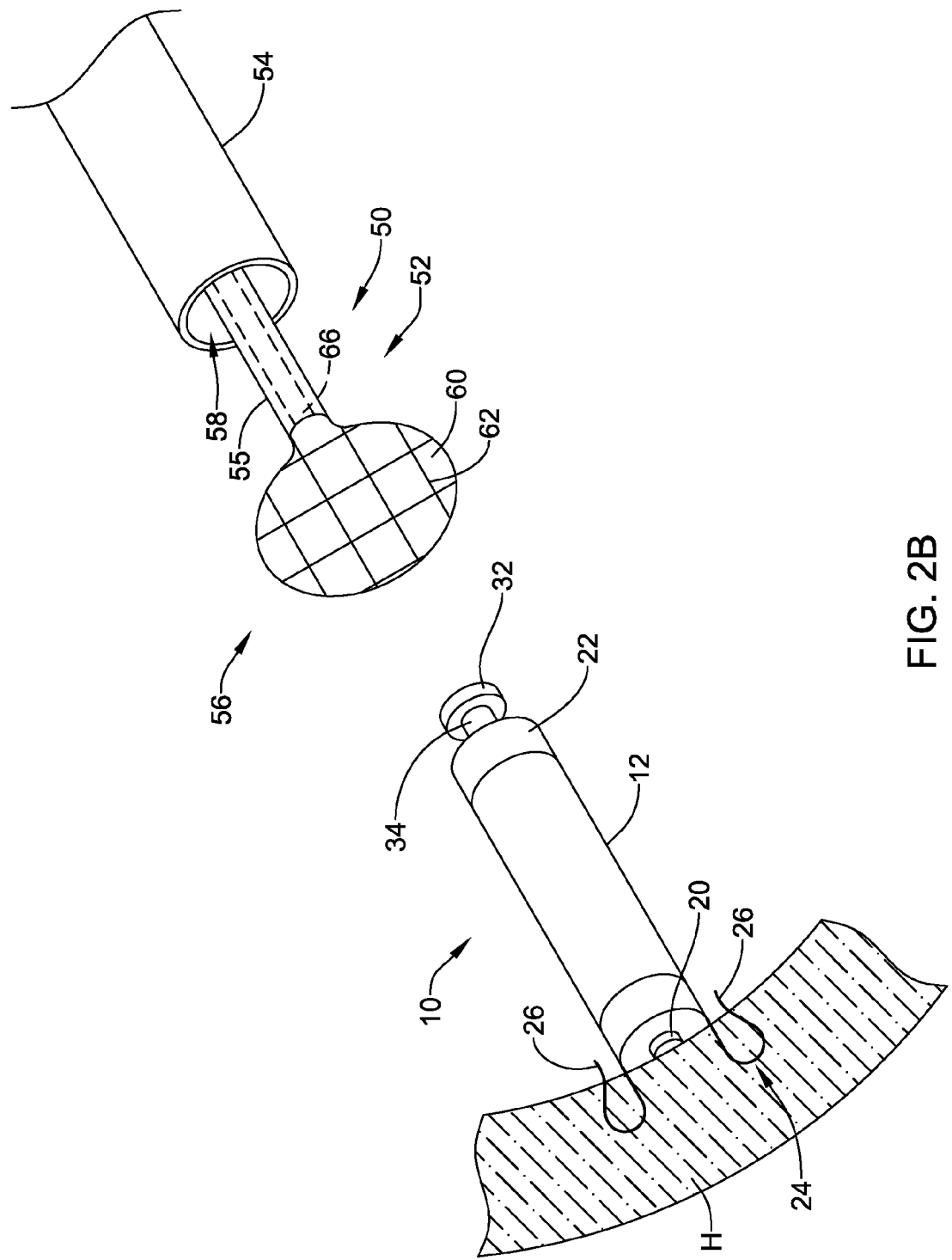

The grasping mechanism 56 may be delivered to the chamber of the heart H with the balloon 60 in a deflated state. As shown in FIG. 2B, the balloon 60 may be inflated to expand the mesh 62 from the first position to the second position. For example, an inflation fluid may be delivered through an inflation lumen 66 extending through the elongate shaft 55 of the retrieval device 52 to the interior of the balloon 60 to inflate the balloon 60. The mesh 62 may be biased toward a contracted configuration in the first position. However, the force exerted on the mesh 62 by the balloon 60 as the balloon 60 is inflated may overcome the biasing forces of the mesh 62 to expand the mesh 62 to the second position. For example, the filaments of the mesh 62 may be formed of an elastomeric material, such as an elastomeric polymeric material, permitting the filaments to stretch or elongate when subjected to the forces applied by the balloon 60. In the absence of the forces applied by the balloon 60, however, the filaments may contract toward the first position.

Figure 2C:
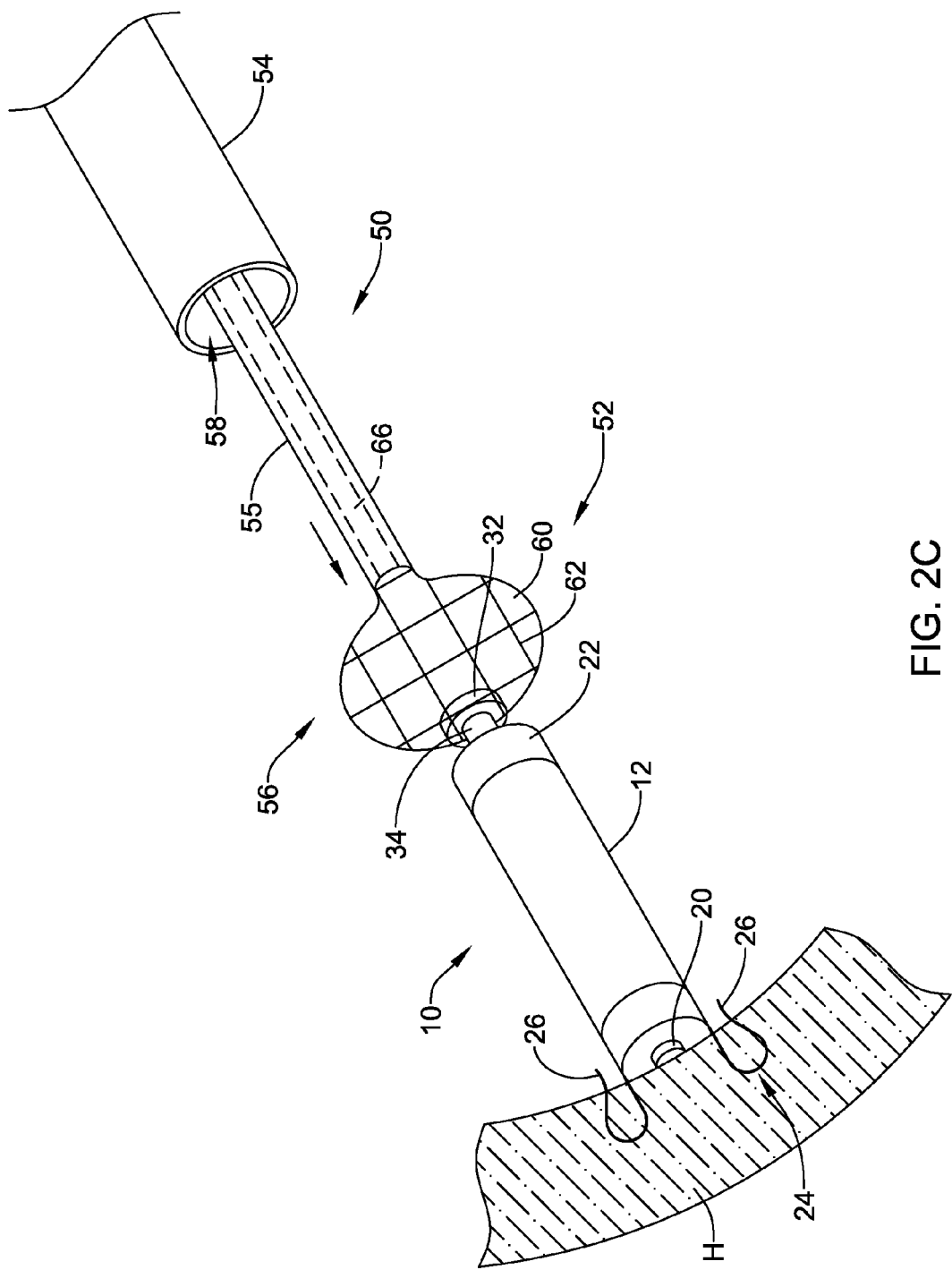

As shown in FIG. 2C, with the grasping mechanism 56 expanded to the second position, the grasping mechanism 56 may be advanced distally toward the docking member 30 of the implantable device 10. As the grasping mechanism 56 engages the docking member 30, the head portion 32 of the docking member 30 may pass through an opening between adjacent filaments of the mesh 62 when the mesh 62 is expanded to the second position. Thus, the head portion 32 may be engaged with the grasping mechanism 56 such that the head portion 32 is positioned within the mesh 62, yet exterior of the balloon 60.

Figure 2D:
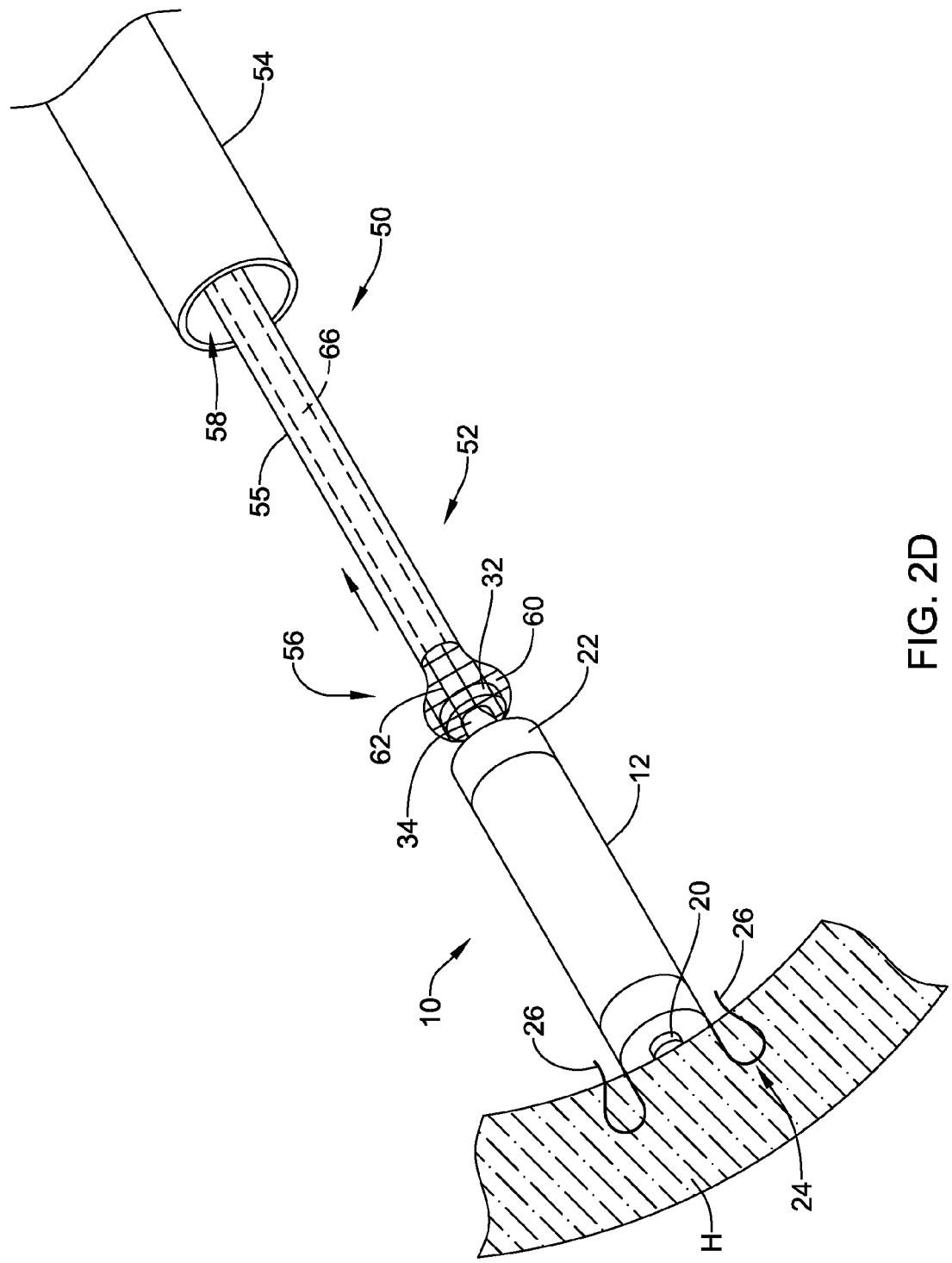

The grasping mechanism 56 may then be contracted toward the first position, as shown in FIG. 2D, to capture the docking member 30 with the grasping mechanism 56. For example, the balloon 60 may then be deflated, as shown in FIG. 2D. Upon deflation of the balloon 60, the mesh 62 may be biased to contract toward the first position to lock the head portion 32 of the docking member 30 in the mesh 62. In other words, as the mesh 62 contracts around the head portion 32, the opening between adjacent filaments through which the head portion 32 is extended through, will be reduced, drawing the filaments into closer contact with the neck portion 34 of the docking member 30. The size of the opening may be reduced to a size less than the size of the head portion 32 such that the head portion 32 cannot pass back out through the opening. Accordingly, contraction of the mesh 62 around the head portion 32 may lock the head portion 32 in the mesh 62. With the head portion 32 locked in the contracted mesh 62, the retrieval device 52 may be actuated proximally relative to the retrieval catheter 54 to draw the implantable cardiac pacing device 10 into the lumen 58 of the retrieval catheter 54. The implantable device 10, retained in the lumen 58 of the retrieval catheter 54 may then be withdrawn from the heart H with the retrieval device 50, by withdrawing the retrieval device 50 proximally.

Another exemplary embodiment of a retrieval device 152 and associate method of retrieving an implantable device 10 is shown in FIGS. 3A-3D. The retrieval device 152 may be extendable distally from a lumen 58 of the retrieval catheter 54 toward the docking member 30 of the implantable device 10. The retrieval device 152 may include an elongate shaft 155 and a grasping mechanism 156 positioned at the distal end of the elongate shaft. The grasping mechanism 156 may be expandable from a first position, shown in FIG. 3A, to a second position, shown in FIG. 3B, and then contracted toward the first position, shown in FIG. 3D, to capture the docking member 30 with the grasping mechanism 156.

The grasping mechanism 156 may include a plurality of expandable struts 160 secured to the distal end of the elongate shaft 155 of the retrieval device 152 and a resilient annular ring 162 attached to the plurality of expandable struts 160, such as the distal ends of the plurality of expandable struts 160. In some instances, the resilient annular ring 162 may lie in a plane perpendicular to the central longitudinal axis of the elongate shaft 155 of the retrieval device 152 and/or may be concentric with the central longitudinal axis of the elongate shaft 155 of the retrieval device 152. In other instances, the resilient annular ring 162 may be arranged in anther desired orientation with respect to the central longitudinal axis of the elongate shaft 155.

Figure 3A:
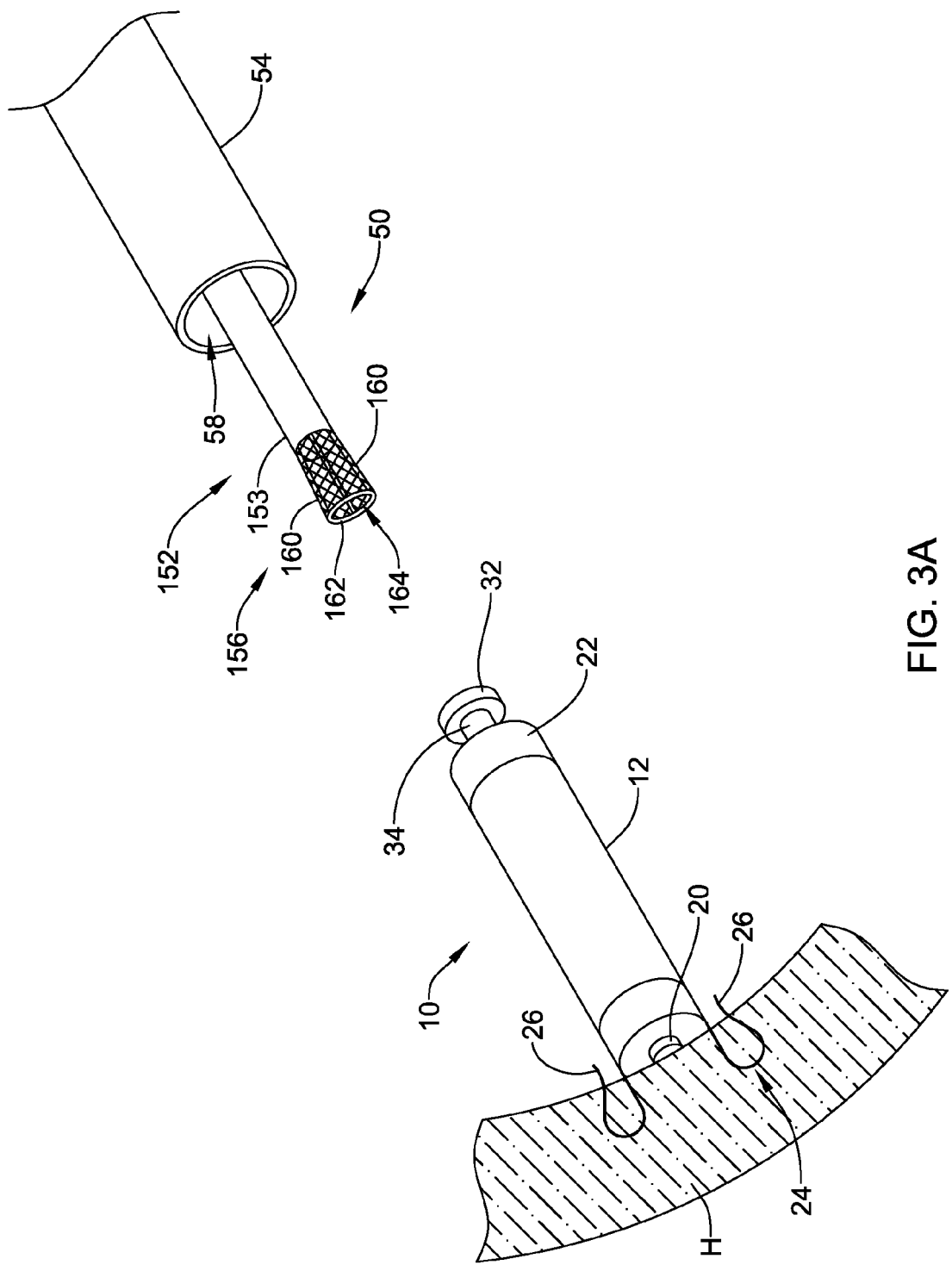
FIGS. 3A-3D are perspective views of another exemplary retrieval device and associate method of retrieving an implantable device.
Figure 3B:
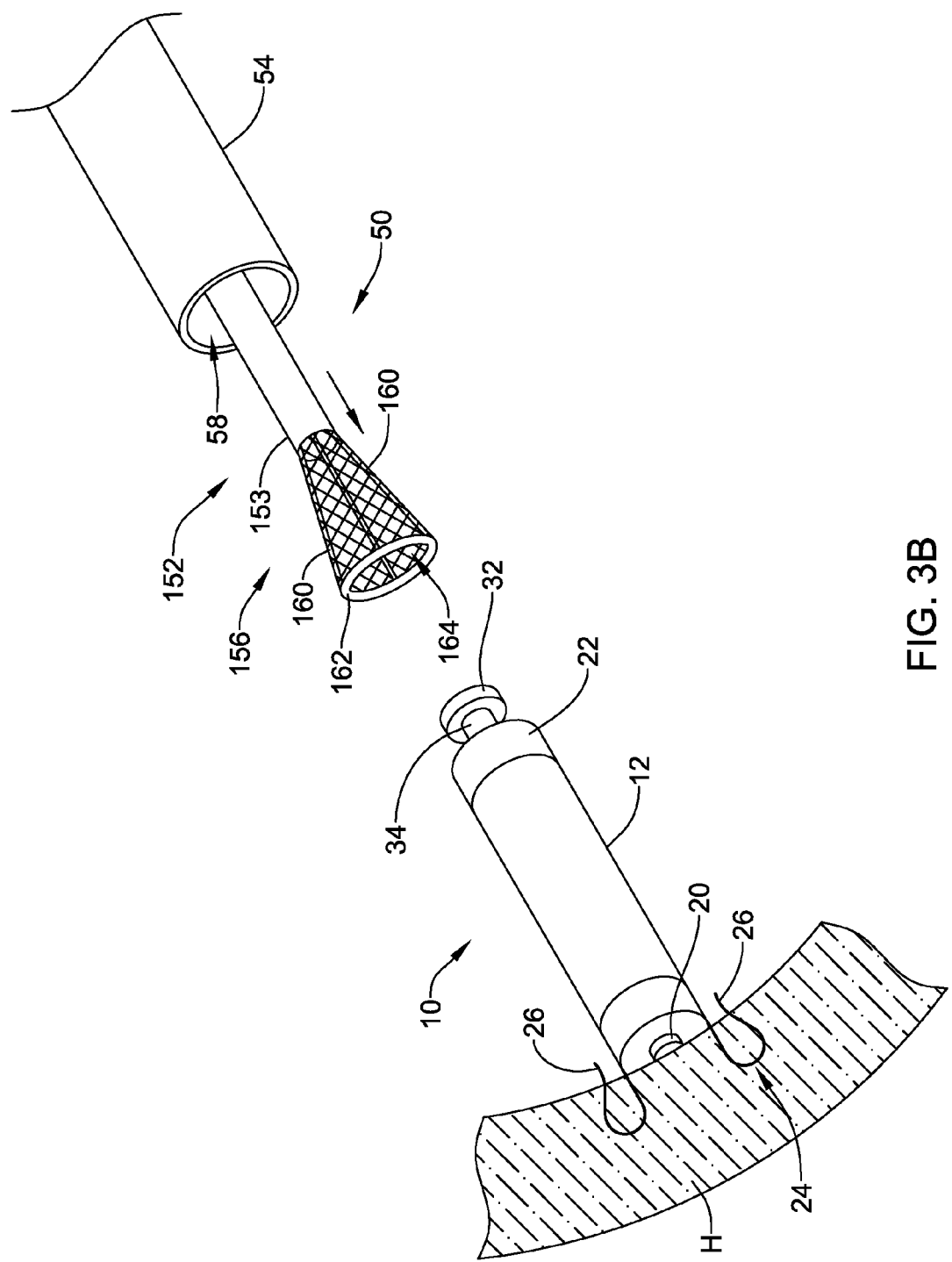

The resilient annular ring 162 may be biased toward a contracted configuration in the first position in which the resilient annular ring 162 may have a first diameter. However, the forces exerted on the resilient annular ring 162 by the radial expansion of the struts 160 in a radially outward direction may overcome the biasing forces of the resilient annular ring 162 to expand the resilient annular ring 162 to the second position, as shown in FIG. 3B, in which the resilient annular ring 162 has a second diameter greater than the first diameter. For example, the resilient annular ring 162 may be formed of an elastomeric material, such as an elastomeric polymeric material, permitting the resilient annular ring 162 to stretch or elongate when subjected to the radially outward forces applied by the struts 160. In the absence of the forces applied by the struts 160, however, the resilient annular ring 162 may contract toward the first position. In other embodiments, the annular ring 162 may be slack or relaxed in the first position.

The expandable struts 160 may be mechanically actuated to radially expand to the second position, or the expandable struts 160 may be biased to automatically radially expand to the expanded second position when unconstrained. Radial expansion of the expandable struts 160 may exert a sufficient force on the resilient annular ring 162 to overcome the biasing forces of the resilient annular ring 162 to expand the resilient annular ring 162 to the second position. In embodiments in which the annular ring 162 is slack or relaxed in the first position, expansion of the expandable struts 160 may enlarge the annular ring 162 to a taut second position.

In some instances the expandable struts 160 may be constrained by an outer tubular member 153 of the retrieval device 152 to allow the resilient annular ring 162 to assume its contracted configuration in the first position. As the outer tubular member 153 is moved proximally relative to the expandable struts 160 to expose the expandable struts 160 from the distal end of the outer tubular member 153 (e.g., by actuating the outer tubular member 153 proximally and/or actuating the expandable struts 160 distally), the expandable struts 160 may automatically radially expand to the expanded second position, stretching the resilient annular ring 162 to the second, enlarged diameter in the second position. In other instances, the expandable struts 160 may be radially expanded via actuation of a push/pull wire extending through the elongate shaft 155, for example, thereby stretching the resilient annular ring 162 to the second, enlarged diameter in the second position. The expandable struts 160 may be formed of any desired material providing the struts 160 with a desired flexibility. For example, the expandable struts 160 may be formed of a polymeric material or a metallic material, such as stainless steel or a nickel-titanium alloy (e.g., nitinol). In some embodiments, the expandable struts 160 may have a memorized expanded shape, such that the expandable struts 160 revert to the memorized expanded shape in the absence of a constraining force.

Figure 3C:
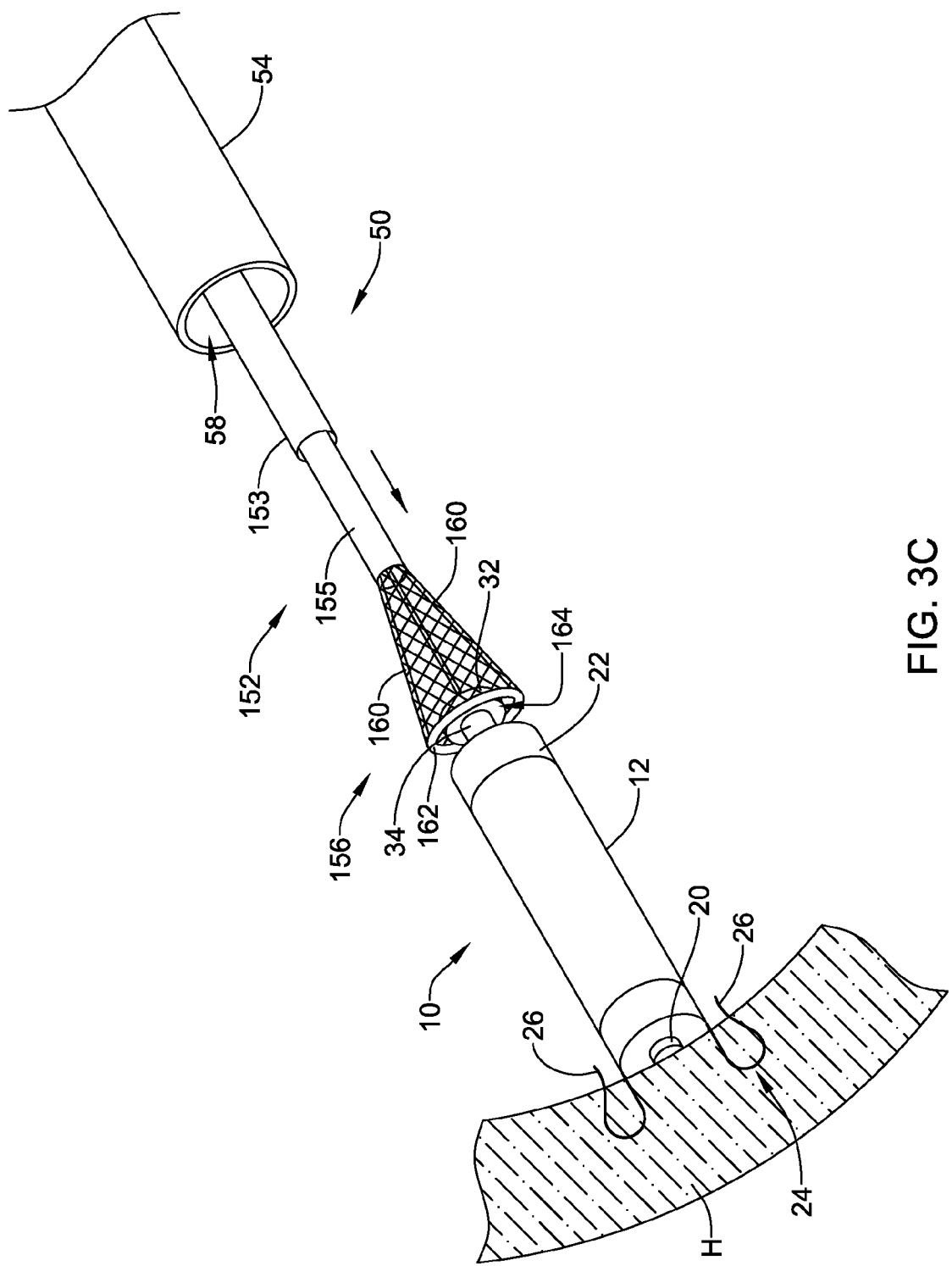

As shown in FIG. 3C, with the grasping mechanism 156 expanded to the second position, the grasping mechanism 156 may be advanced distally toward the docking member 30 of the implantable device 10. As the grasping mechanism 156 engages the docking member 30, the head portion 32 of the docking member 30 may pass through an opening 164 through the resilient annular ring 162 when the resilient annular ring 162 is expanded to the second position. Thus, the head portion 32 may be engaged with the grasping mechanism 156 such that the head portion 32 is positioned through the opening 164 of the resilient annular ring 162 to a position proximal of the resilient annular ring 162. In some embodiments, such as the embodiment shown in FIGS. 3A-3D, the grasping mechanism 156 may include a mesh covering the openings between adjacent expandable struts 160, preventing inadvertent or unintentional positioning of the head portion 32 of the docking member 30 through the openings between adjacent struts 160. Accordingly, the mesh may ensure that the docking member 30 is engaged with the grasping mechanism 156 through the opening 164.

Figure 3D:
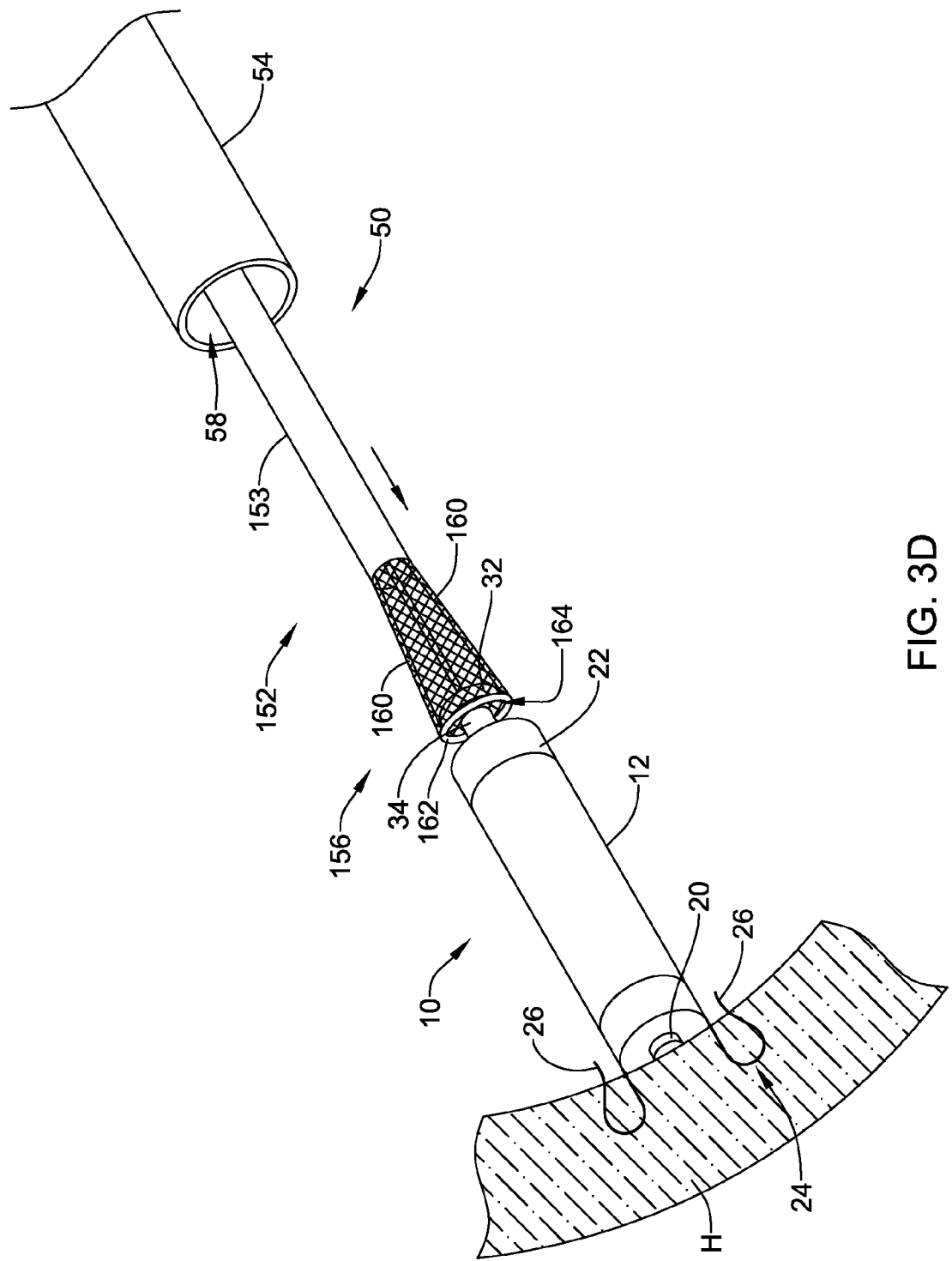

The grasping mechanism 156 may then be contracted toward the first position, as shown in FIG. 3D, to capture the docking member 30 with the grasping mechanism 156. For example, the outer tubular member 153 may be moved distally relative to the expandable struts 160 to direct the expandable struts 160 into the distal end of the outer tubular member 153 (e.g., by actuating the outer tubular member 153 distally and/or actuating the expandable struts 160 proximally). The forces acting on the expandable struts 160 by the outer tubular member 153 may cause the expandable struts 160 to radially contract toward the contracted first position, permitting the resilient annular ring 162 to revert toward the contracted, first diameter in the first position. In other instances, the expandable struts 160 may be radially contracted via actuation of a push/pull wire extending through the elongate shaft 155, for example, thereby permitting the resilient annular ring 162 to revert toward the contracted, first diameter in the first position. In other words, as the expandable struts 160 are radially contracted, the resilient annular ring 162 will contract toward its equilibrium configuration, reducing the diameter of the opening 164 through which the head portion 32 is extended through, drawing the resilient annular ring 162 into closer contact with the neck portion 34 of the docking member 30. The diameter of the opening 164 of the resilient annular ring 162 may be reduced to a size less than the diameter of the head portion 32 such that the head portion 32 cannot pass back out through the opening 164. Accordingly, contraction of the resilient annular ring 162 around the head portion 32 may lock the head portion 32 in the grasping mechanism 156. With the head portion 32 locked in the grasping mechanism 156 with the contracted resilient annular ring 162, the retrieval device 152 may be actuated proximally relative to the retrieval catheter 54 to draw the implantable cardiac pacing device 10 into the lumen 58 of the retrieval catheter 54. The implantable device 10, retained in the lumen 58 of the retrieval catheter 54 may then be withdrawn from the heart H with the retrieval device 50, by withdrawing the retrieval device 50 proximally.

Another exemplary embodiment of a retrieval device 252 and associate method of retrieving an implantable device 10 is shown in FIGS. 4A-4D. The retrieval device 252 may be extendable distally from a lumen 58 of the retrieval catheter 54 toward the docking member 30 of the implantable device 10. The retrieval device 252 may include an elongate shaft 255 and a grasping mechanism 256 positioned at the distal end of the elongate shaft 255. The grasping mechanism 256 may be expandable from a first position, shown in FIG. 4A, to a second position, shown in FIG. 4B, and then contracted toward the first position, shown in FIG. 4D, to capture the docking member 30 with the grasping mechanism 256.

The grasping mechanism 256 may include an inflatable balloon 260 secured to the distal end of the elongate shaft 255 of the retrieval device 252 and a resilient annular ring 262 extending around a distal rim of the balloon 260. The inflatable balloon 260 may include an annular portion defining a distal opening 264 extending proximally into the balloon 260 through the resilient annular ring 262. In some embodiments, as shown in FIG. 4B, the inflatable balloon 260 may include an annular portion defining a distal opening extending proximally into the balloon 260 when inflated. In some instances, the inflatable balloon 260 may be conically shaped, flaring outward in a distal direction from the elongate shaft 255.

In some instances, the resilient annular ring 262 may be a monolithic portion of the material of the balloon 260, however, in other instances the resilient annular ring 262 may be a discrete member attached to the balloon 260. The resilient annular ring 262 may lie in a plane perpendicular to the central longitudinal axis of the elongate shaft 255 of the retrieval device 252 and/or may be concentric with the central longitudinal axis of the elongate shaft 255 of the retrieval device 252. In other instances, the resilient annular ring 262 may be arranged in anther desired orientation with respect to the central longitudinal axis of the elongate shaft 255.

The resilient annular ring 262 may be biased toward a contracted configuration in the first position in which the resilient annular ring 262 may have a first diameter. However, the forces exerted on the resilient annular ring 262 by inflation of the balloon 260 may overcome the biasing forces of the resilient annular ring 262 to expand the resilient annular ring 262 to the second position, as shown in FIG. 4B, in which the resilient annular ring 262 has a second diameter greater than the first diameter. For example, the resilient annular ring 262 may be formed of an elastomeric material, such as an elastomeric polymeric material, permitting the resilient annular ring 262 to stretch or elongate when subjected to the radial outward forces applied by inflation of the balloon 260. In the absence of the inflation forces applied by the inflated balloon 260, however, the resilient annular ring 262 may contract toward the first position.

The grasping mechanism 256 may be delivered to the chamber of the heart H with the balloon 260 in a deflated state. As shown in FIG. 4B, the balloon 260 may be inflated to expand or stretch the resilient annular ring 262 from the first position to the second position. For example, an inflation fluid may be delivered through an inflation lumen 266 extending through the elongate shaft 255 of the retrieval device 252 to the interior of the balloon 260 to inflate the balloon 260. The resilient annular ring 262 may be biased toward a contracted configuration in the first position. However, the force exerted on the resilient annular ring 262 by the balloon 260 as the balloon 260 is inflated may overcome the biasing forces of the resilient annular ring 262 to expand the resilient annular ring 262 to the second position. For example, the resilient annular ring 262 may be formed of an elastomeric material, such as an elastomeric polymeric material, permitting the resilient annular ring 262 to stretch or elongate when subjected to the radially outward forces applied by inflating the balloon 160. In the absence of the forces applied by inflating the balloon 260, however, the resilient annular ring 262 may contract toward the first position.

Figure 4A:
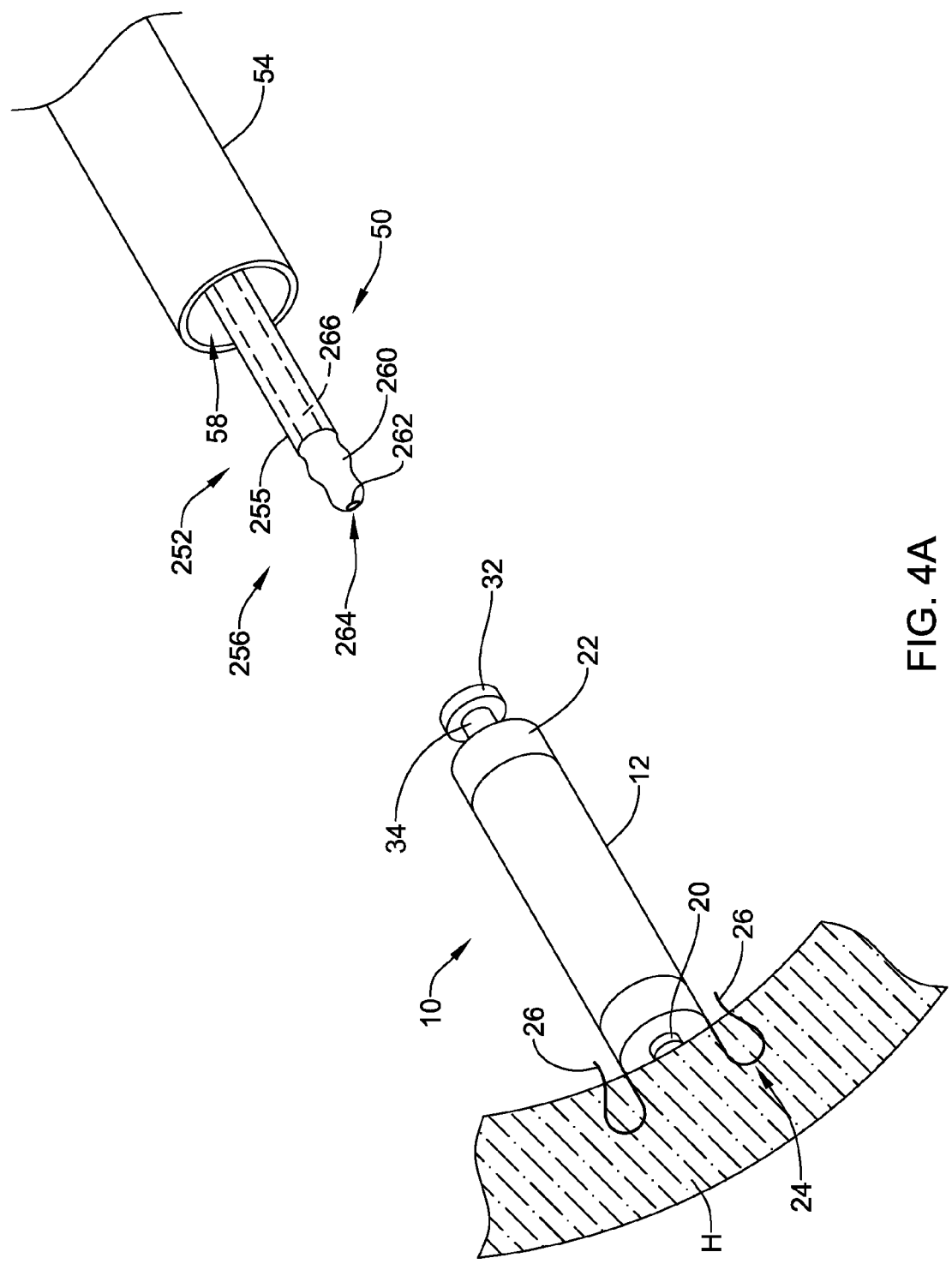
Figure 4C:
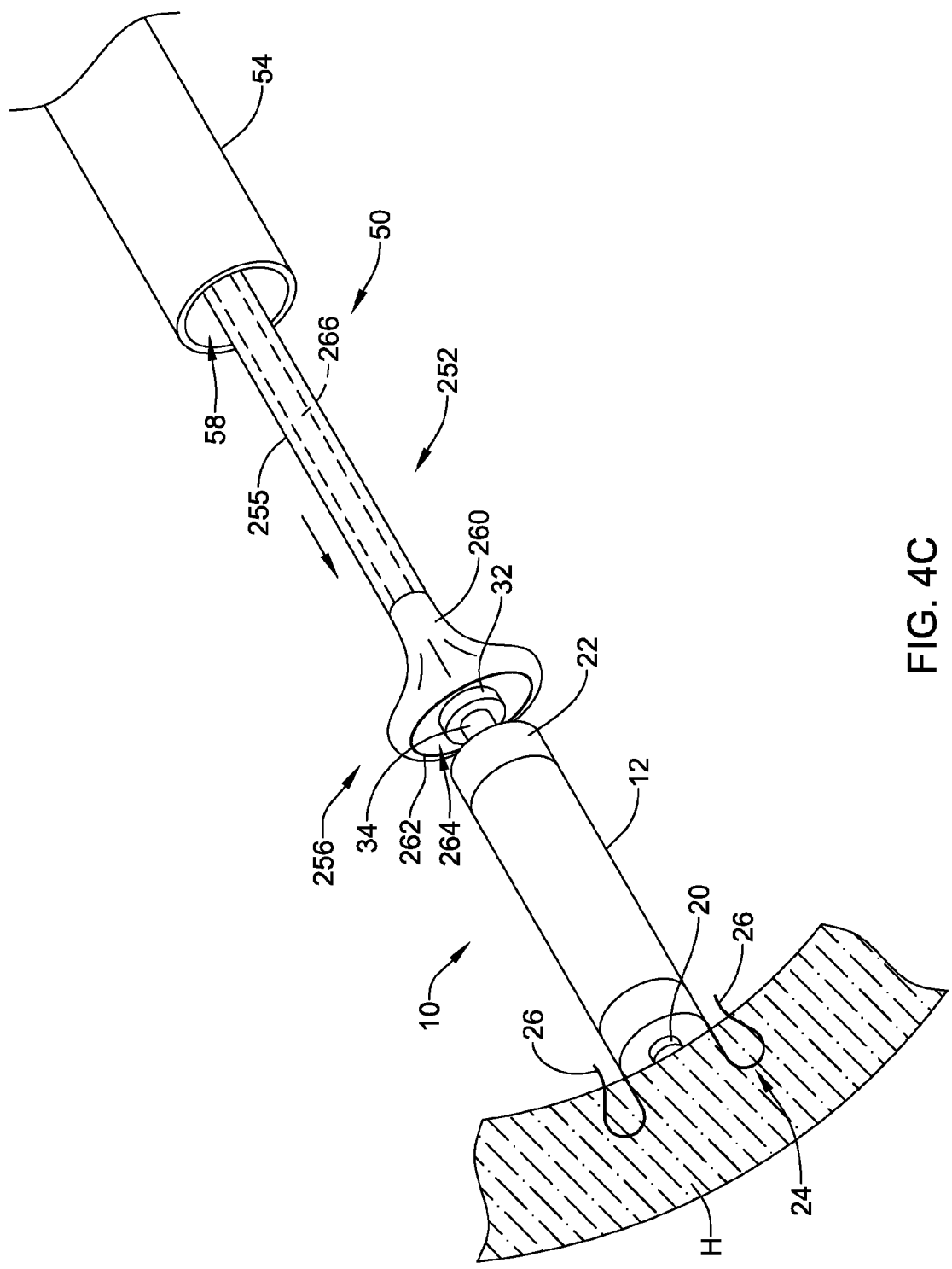

As shown in FIG. 4C, with the grasping mechanism 256 expanded to the second position, the grasping mechanism 256 may be advanced distally toward the docking member 30 of the implantable device 10. As the grasping mechanism 256 engages the docking member 30, the head portion 32 of the docking member 30 may pass through the opening 264 through the resilient annular ring 262 when the resilient annular ring 262 is expanded to the second position. Thus, the head portion 32 may be engaged with the grasping mechanism 256 such that the head portion 32 is positioned through the opening 264 of the resilient annular ring 262 to a position proximal of the resilient annular ring 262.

Figure 4D:
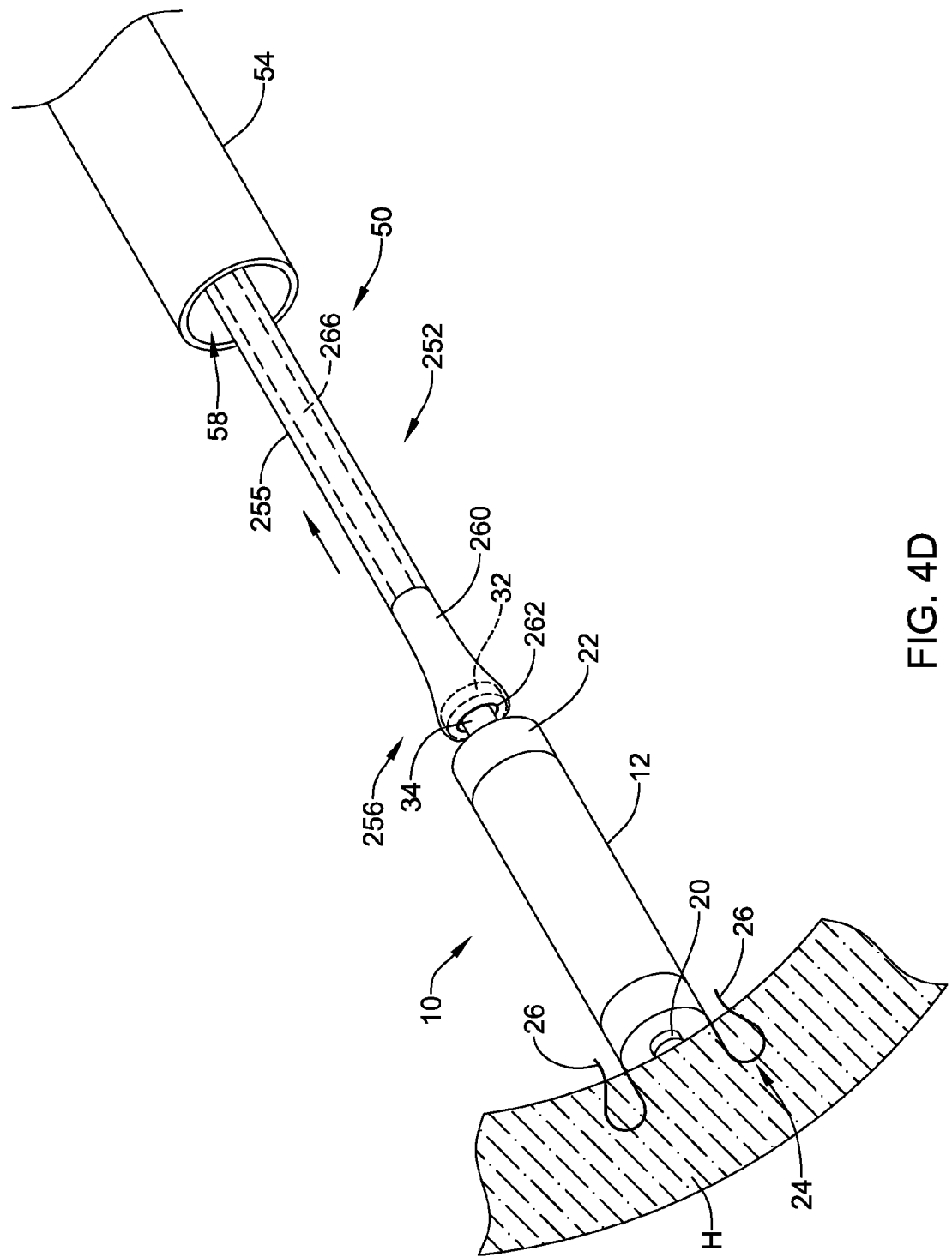

The grasping mechanism 256 may then be contracted toward the first position, as shown in FIG. 4D, to capture the docking member 30 with the grasping mechanism 256. For example, the balloon 260 may then be deflated, as shown in FIG. 4D. Upon deflation of the balloon 260, the resilient annular ring 262 may be biased to contract toward the first position to lock the head portion 32 of the docking member 30 within the opening 264 extending into the balloon 260 proximal of the resilient annular ring 262. In other words, as the balloon 260 is deflated, the resilient annular ring 262 will contract toward its equilibrium configuration, reducing the diameter of the opening 264 through which the head portion 32 is extended through, drawing the resilient annular ring 262 into closer contact with the neck portion 34 of the docking member 30. The diameter of the opening 264 of the resilient annular ring 262 may be reduced to a size less than the diameter of the head portion 32 such that the head portion 32 cannot pass back out through the opening 264. Accordingly, contraction of the resilient annular ring 262 around the head portion 32 may lock the head portion 32 in the grasping mechanism 256. With the head portion 32 locked in the grasping mechanism 256 with the contracted resilient annular ring 262, the retrieval device 252 may be actuated proximally relative to the retrieval catheter 54 to draw the implantable cardiac pacing device 10 into the lumen 58 of the retrieval catheter 54. The implantable device 10, retained in the lumen 58 of the retrieval catheter 54 may then be withdrawn from the heart H with the retrieval device 50, by withdrawing the retrieval device 50 proximally.

Figure 5A:
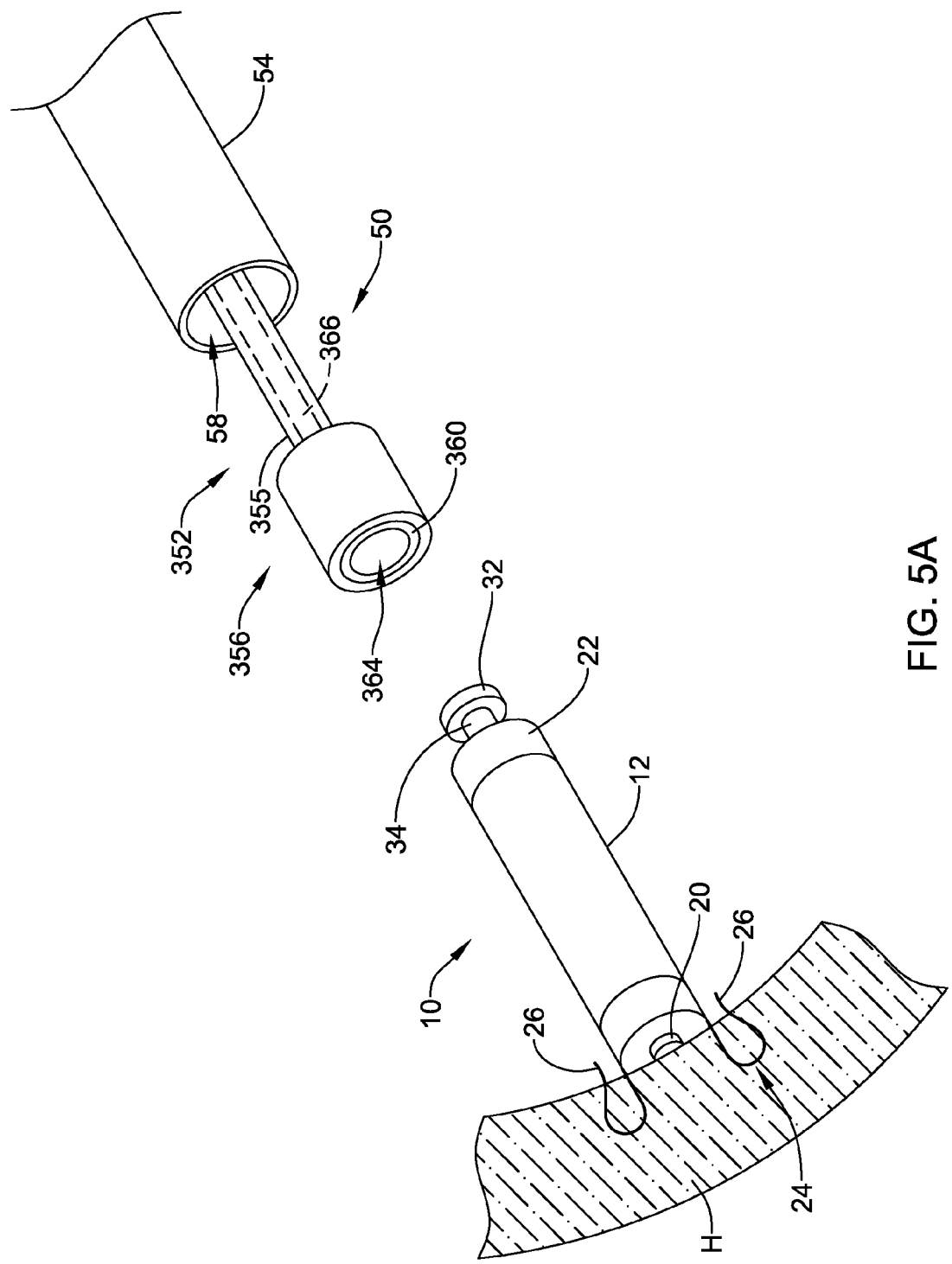
FIGS. 5A-5C are perspective views of another exemplary retrieval device and associate method of retrieving an implantable device.
Figure 5B:
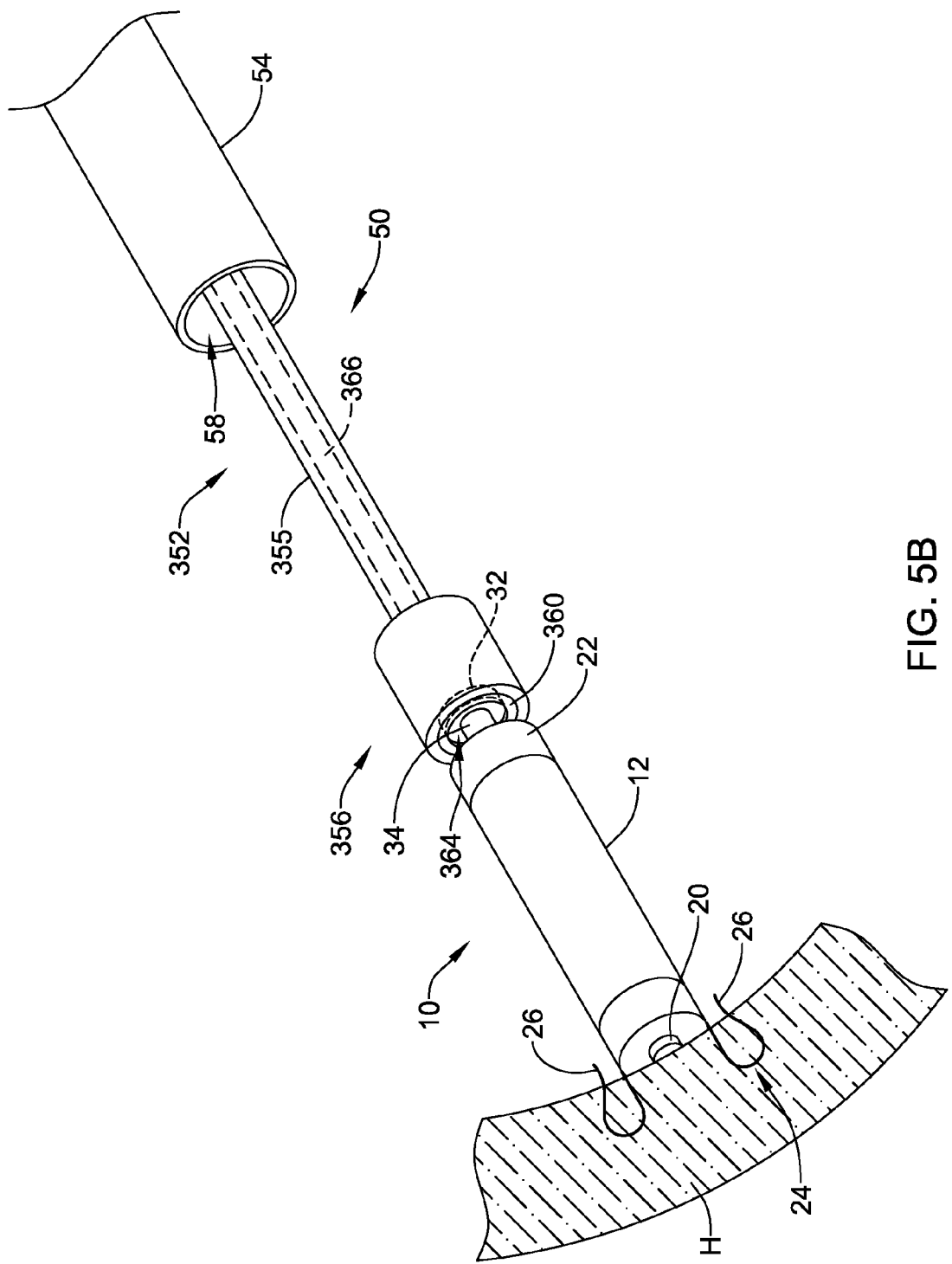
Figure 5C:
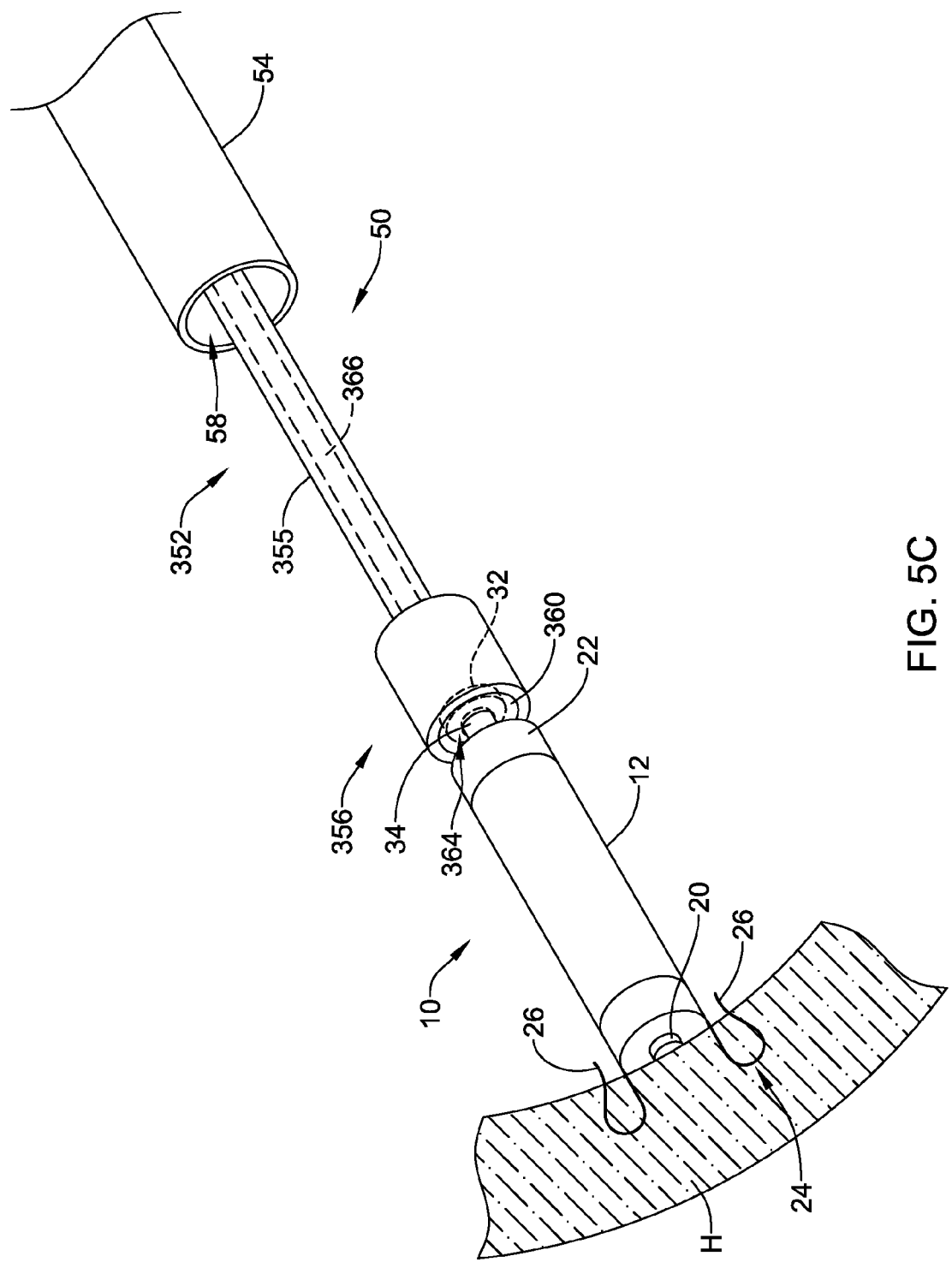

Another exemplary embodiment of a retrieval device 352 and associate method of retrieving an implantable device 10 is shown in FIGS. 5A-5C. The retrieval device 352 may be extendable distally from a lumen 58 of the retrieval catheter 54 toward the docking member 30 of the implantable device 10. The retrieval device 352 may include an elongate shaft 355 and a grasping mechanism 356 positioned at the distal end of the elongate shaft 355. The grasping mechanism 356 may be actuatable from a first position, shown in FIG. 5A, to a second position, shown in FIG. 5C, to capture the docking member 30 with the grasping mechanism 356.

The grasping mechanism 356 may include an inflatable balloon 360 secured within the distal end of the elongate shaft 355 of the retrieval device 352. The inflatable balloon 360, which may be an annular balloon, may include an annular portion defining a distal opening 364 extending proximally into the balloon 360. The opening 364 into the annular balloon 360 may have a first diameter in a deflated state, and the opening 364 into the annular balloon 360 may have a second diameter in an inflated state, the second diameter being less than the first diameter. In other words, the balloon 360 may inflate radially inward when inflated, contracting the opening 364.

The grasping mechanism 356 may be delivered to the chamber of the heart H with the balloon 360 in a deflated state, as shown in FIG. 5A. The grasping mechanism 356 may be advanced distally toward the docking member 30 of the implantable device 10 with the balloon 360 in the deflated state. As the grasping mechanism 356 engages the docking member 30, the head portion 32 of the docking member 30 may pass into or through the opening 364 of the balloon 360, as shown in FIG. 5B.

As shown in FIG. 5C, the balloon 360 may be inflated by delivering inflation fluid through the inflation lumen 366 to the balloon 360 to contract the balloon 360 around the head portion 32 and/or neck portion 34 of the docking member 30, to capture the docking member 30 with the grasping mechanism 356. In other words, inflation of the balloon 360 may cause the balloon 360 to expand radially inward, reducing the diameter of the opening 364 through which the head portion 32 is extended through, drawing the annular balloon 360 into closer contact with the head portion 32 and/or neck portion 34 of the docking member 30. The diameter of the opening 364 of the balloon 360 may be reduced to a size less than the diameter of the head portion 32 such that the head portion 32 cannot pass back out through the opening 364. Accordingly, contraction of the annular balloon 360 around the head portion 32 may lock the head portion 32 in the grasping mechanism 356 while the balloon 360 is inflated. With the head portion 32 locked in the grasping mechanism 356 with the inflated annular balloon 360, the retrieval device 352 may be actuated proximally relative to the retrieval catheter 54 to draw the implantable cardiac pacing device 10 into the lumen 58 of the retrieval catheter 54. The implantable device 10, retained in the lumen 58 of the retrieval catheter 54 may then be withdrawn from the heart H with the retrieval device 50, by withdrawing the retrieval device 50 proximally.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An assembly for retrieving an implantable cardiac pacing device, comprising:
   an implantable cardiac pacing device having a housing, an electrode positioned proximate a distal end of the housing, and a docking member extending from a proximal end of the housing opposite the distal end, the docking member including a head portion and a neck portion extending between the housing and the head portion; and
   a retrieval system including:
      a retrieval catheter having a proximal end, a distal end, and a lumen extending into the retrieval catheter from the distal end; and
      a retrieval device advanceable from the distal end of the retrieval catheter, the retrieval device having a grasping mechanism configured to capture the docking member to draw the implantable cardiac pacing device into the lumen of the retrieval catheter;
   wherein the grasping mechanism is expandable from a first position to a second position, the grasping mechanism being biased toward the first position in an equilibrium condition;
   wherein the grasping mechanism is configured to surround and pass over the head portion of the docking member in the second position, and be contracted toward the first position to capture the docking member with the grasping mechanism;
   wherein the grasping mechanism includes an inflatable balloon;
   wherein the inflatable balloon includes an annular portion defining a distal opening extending proximally into the balloon; and
   wherein the inflatable balloon includes a resilient annular ring extending around a rim of the distal opening.

2. The assembly of claim 1, wherein the inflatable balloon is conical shaped.

3. The assembly of claim 1, wherein the balloon is inflatable to expand the resilient annular ring to the second position to permit the head portion of the docking member to pass through the resilient annular ring into the distal opening of the balloon.

4. The assembly of claim 3, wherein upon deflation of the balloon, the resilient annular ring is biased to contract toward the first position around the neck portion of the docking member to lock the docking member in the annular portion of the balloon.

5. The assembly of claim 1, wherein the retrieval device includes an inflatable lumen configured to delivery inflation fluid to the inflatable balloon.

6. An assembly for retrieving an implantable cardiac pacing device, comprising:
   an implantable cardiac pacing device having a housing, an electrode positioned proximate a distal end of the housing, and a docking member extending from a proximal end of the housing opposite the distal end, the docking member including a head portion and a neck portion extending between the housing and the head portion; and
   a retrieval system including:
      a retrieval catheter having a proximal end, a distal end, and a lumen extending into the retrieval catheter from the distal end; and
      a retrieval device advanceable from the distal and of the retrieval catheter, the retrieval device having a grasping mechanism configured to capture the docking member to draw the implantable cardiac pacing device into the lumen of the retrieval catheter;
   wherein the grasping mechanism is expandable from a first position to a second position, the grasping mechanism being biased toward the first position in an equilibrium condition;
   wherein the grasping mechanism is configured to surround and pass over the head portion of the docking member in the second position; and be contracted toward the first position to capture the docking member with the grasping mechanism;
   wherein the grasping mechanism includes an inflatable balloon and a mesh formed of a plurality of filaments surrounding the balloon.

7. The assembly of claim 6, wherein the balloon is inflatable to expand the mesh to the second position to permit the head portion of the docking member to pass through an opening between adjacent filaments of the mesh.

8. The assembly of claim 7, wherein upon deflation of the balloon, the mesh is biased to contract toward the first position to lock the head portion of the docking member in the mesh.

9. An assembly for retrieving an implantable cardiac pacing device, comprising:
   an implantable cardiac pacing device having a housing, an electrode positioned proximate a distal end of the housing, and a docking member extending from a proximal end of the housing opposite the distal end, the docking member including a head portion and a neck portion extending between the housing and the head portion; and
   a retrieval system including:
      a retrieval catheter having a proximal end, a distal end, and a lumen extending into the retrieval catheter from the distal end; and
      a retrieval device advanceable from the distal end of the retrieval catheter, the retrieval device having a grasping mechanism configured to capture the docking member to draw the implantable cardiac pacing device into the lumen of the retrieval catheter:
   wherein the grasping mechanism is expandable from a first position to a second position, the grasping mechanism being biased toward the first position in an equilibrium condition;
   wherein the grasping mechanism is configured to surround and pass over the head portion of the docking member in the second position, and be contracted toward the first position to capture the docking member with the grasping mechanism; and
   wherein the grasping mechanism includes a plurality of expandable struts and a resilient annular ring attached to the plurality of expandable struts.

10. The assembly of claim 9, wherein the plurality of struts are expandable to expand the resilient annular ring to the second position to permit the head portion of the docking member to pass proximally through the resilient annular ring.

11. The assembly of claim 10, wherein the resilient annular ring is biased to contract toward the first position around the neck portion of the docking member to lock the grasping mechanism to the docking member.

12. The assembly of claim 9, further comprising a mesh covering opening between adjacent struts.

* * * * *